United States Patent
Lei et al.

(10) Patent No.: US 10,508,345 B2
(45) Date of Patent: Dec. 17, 2019

(54) SENSOR IN AN INTERNET-OF-THINGS AND MANUFACTURING METHOD OF THE SAME

(71) Applicant: TAIWAN SEMICONDUCTOR MANUFACTURING COMPANY LTD., Hsinchu (TW)

(72) Inventors: Ming-Ta Lei, Hsin-Chu (TW); Chia-Hua Chu, Hsinchu County (TW); Hsin-Chih Chiang, Hsinchu (TW); Tung-Tsun Chen, Hsinchu (TW); Chun-Wen Cheng, Hsinchu County (TW)

(73) Assignee: TAIWAN SEMICONDUCTOR MANUFACTURING COMPANY LTD., Hsinchu (TW)

( * ) Notice: Subject to any disclaimer, the term of this patent is extended or adjusted under 35 U.S.C. 154(b) by 142 days.

(21) Appl. No.: 14/879,018

(22) Filed: Oct. 8, 2015

(65) Prior Publication Data
US 2017/0102353 A1    Apr. 13, 2017

(51) Int. Cl.
*C23F 4/00*     (2006.01)
(52) U.S. Cl.
CPC ...................................... *C23F 4/00* (2013.01)
(58) Field of Classification Search
CPC ............. G01N 27/128; G01N 33/0075; G01N 27/4067
USPC ........................................................ 73/31.05
See application file for complete search history.

(56) References Cited

U.S. PATENT DOCUMENTS

2014/0260546 A1* 9/2014 Chen .................... G01N 27/128
                                                            73/31.06

* cited by examiner

*Primary Examiner* — John Fitzgerald
*Assistant Examiner* — Rodney T Frank
(74) *Attorney, Agent, or Firm* — WPAT, P.C., Intellectual Property Attorneys; Anthony King (57) ABSTRACT

Some embodiments of the present disclosure provide a gas sensor in an IOT. The gas sensor includes a substrate, a conductor disposed above the substrate, and a sensing film disposed over the conductor. The conductor has a top-view pattern including a plurality of openings, a minimal dimension of the opening being less than about 4 micrometer; and a perimeter enclosing the opening. Some embodiments of the present disclosure provide a method of manufacturing a gas sensor. The method includes receiving a substrate; forming a conductor, over the substrate; patterning the conductor to form a plurality of openings in the conductor by an etching operation, and forming a gas-sensing film over the conductor. The openings are arranged in a repeating pattern, and a minimal dimension of the opening being about 4 micrometer.

20 Claims, 13 Drawing Sheets

SENSOR IN AN INTERNET-OF-THINGS AND MANUFACTURING METHOD OF THE SAME

FIELD

The present disclosure relates to a sensor in an internet-of-things (IOT), the sensor including a built-in heating element.

BACKGROUND

The Internet-of-Things (IoT) is the interconnection of various embedded devices. Such devices (called "things") may or may not have user-accessible input/output capability. For example, a thing may be an embedded sensor inside of a product such as a refrigerator or washing machine. Such a thing may not have a mouse, keyboard, display or any other type of user-accessible device by which a person can digitally interact with the thing.

A portable sensor connected in an IOT can be used for various applications taking advantage of its compactability. In the course of developing various types of the gas sensor, they have been modified to meet the purpose of use and detection of a certain desired gas: through improvements on employed materials and applicable sensing apparatuses. As a result of these efforts, various types of the gas sensor have been commercialized to be used in industries, medical fields and daily lives. Particularly, wide distribution of liquefied natural gas (LNG) and liquefied petroleum gas (LPG) and public attention to socially issued problems of drunk driving and personal hygiene has led the gas sensor to be further commercialized in different types such as a portable leaking gas sensor, a portable alcohol analyzer, or a portable breath analyzer.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Semiconductor is classified into an n-type and a p-type depending on conductivity mechanisms. Tin dioxide ($SnO_2$), which is the most typical sensitizer, is one of the n-type semiconductors. The number of positive ions of Sn is quantitatively less than that of negative ions of O and thus, producing unpaired electrons which contribute to a degree of conductivity. This $SnO_2$ then adsorbs oxygen in atmosphere to balance the number of positive and negative ions. Because of anionic characteristics of the adsorbed oxygen, electrons contributing to the conductivity of the semiconductor become locally captured in a surface of the adsorbed oxygen. As a result of this capturing state, the electrons lose their conductivity.

If the $SnO_2$ with the adsorbed oxygen is exposed to a reduction gas, e.g., CO and ammonia ($NH_3$), the adsorbed oxygen react with such reduction gas and become desorbed from the $SnO_2$ as shown in the following chemical equation.

$$2CO + O_2 \rightarrow 2CO_2 \qquad \text{Eq. 1}$$

As shown in the Eq. 1, the captured electrons become free and contribute to the conductivity. Therefore, a specific gas type to be detected determines a degree of the conductivity of a semiconductor sensor. The detection of changes in the conductivity degree provides information on the presence or absence of a specific desired gas and its concentration if presents. Such material as platinum (Pt), gold (Au) and silver (Ag) are also added to the sensitizer $SnO_2$ as a catalyst in order to increase a sensing ability.

Apart from the semiconductor materials on the sensor, temperature control for the sensing region is a crucial technique in a portable sensor. Certain chemical reaction can be significantly accelerated under a temperature greater than ambient temperature, especially when the target to be sensed is low in concentration. A heating element is usually a built-in component in a gas sensor in order to generate an elevated temperature in proximity to the chemical reaction zone in order to foster the chemical reaction and thus the sensitivity. Certainly excessive elevated temperature may inhibit particular chemical reactions. Also designing the heating element in a sensor being a component of an IOT, the power-consumption of the sensor shall be as low as possible. Conventionally a serpentine-shaped, a C-shaped, and a spiral-shaped heating element are utilized in the gas sensor. However, the displacement of the aforesaid heating elements is too great to an extent that limits the operating lifetime of the sensor. For example, a spiral-shaped heating element can generate serious in-plane or out-of-plane deformation after thousands of hours of operation.

Conventionally, different heating element patterns can be implemented (e.g., C-shaped, spiral, or serpentine patterns) in order to yield the ideal thermal distribution on the device. The heat can be generated by Joule heating (Heat=Power*Time=Current$^2$*Resistance*Time). The heating current may be voltage or current controlled and delivered in pulses or in a constant manner. The heating current may be delivered by simple current splitting or by individual (current or voltage) output to the heating elements. Joule heating relies on the resistance of heating elements, and the resistance can be designed by varying path lengths that current travels. For example, a spiral shape (from a top view of a heating element) is widely adopted as a general pattern of the heating element due to the fact that the pattern is easy to fabricate with a lift-off operation. The spiral-shaped pattern is composed of one conductive path spiraling in a circular or a polygonal fashion. One end of the spiral-shaped pattern is connected to a voltage source and the other end of the spiral-shaped pattern is grounded. A dimension of a spiral-shaped heating element, however, can only be limited to the order or centimeter or millimeter. It is difficult to shrink the dimension of the spiral-shaped heating element using lift-off technique, and thus the conventional heating element is hard to incorporate into a portable device in light of shrinked real estate in the portable device while same thermal efficiency shall be maintained.

The present disclosure provides a gas sensor in an IOT having a special heating element pattern from a top view which can effectively reduce the displacement or deformation after conventional operation lifetime limit. Thermal efficiency, power consumption, and a dimension of the gas sensor are also improved or shrinked due to the adoption of the heating element pattern described herein. The displacement referred herein is directed to a deformation measurement of a planar material in the vertical direction perpendicular to the plane.

Figure 1:
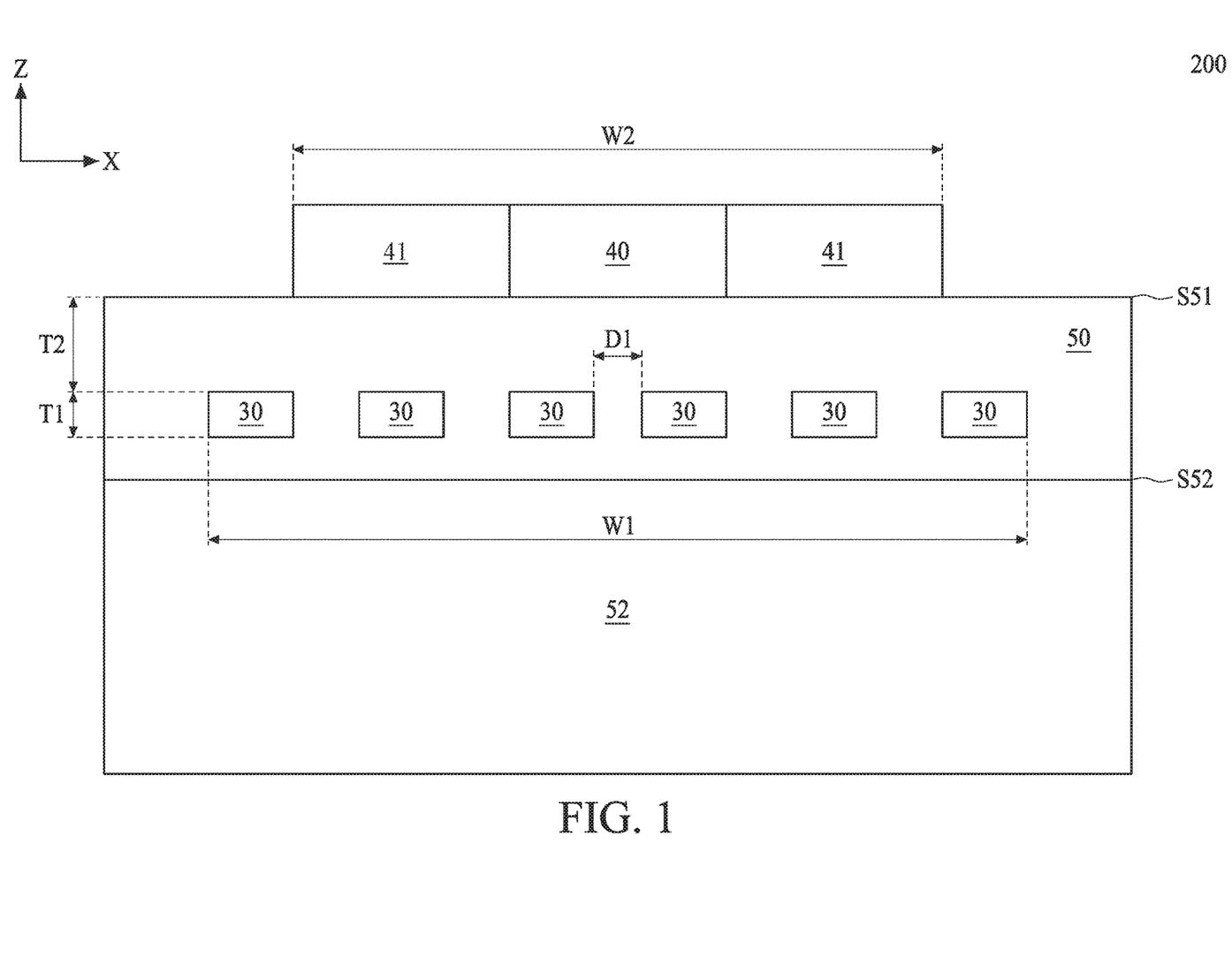
FIG. 1 is a cross-sectional view of a gas sensor, in accordance with some embodiments of the present disclosure.

Referring to FIG. 1, FIG. 1 is a cross-sectional view of a gas sensor 200, in accordance with some embodiments of the present disclosure. In the cross section, several conductors 30 are embedded in an insulator 50. The conductors 30 and the insulator 50 are positioned over a substrate 52. In some embodiments, the substrate 52 can be made of porous materials or materials with low thermal conductivity in order to reduce the heat dissipation through the substrate 52. In other words, porous substrate may have lower thermal conductivity compared to the non-porous counterpart since air filling the pores or cavities may have lower thermal conductivity than that of the substrate materials. Note the term "heating element" and "conductors" refer to the same element in the present disclosure. In some embodiments, a critical dimension of a distance D1 between adjacent conductors 30 is less than about 4 micrometer. The conductors 30 can be connected to a voltage source or a current source and become a heater devised to affect the temperature at a sensing film 40 disposed above the insulator 50. Sensing electrode 41 is positioned in proximity to the sensing film 40. Sensing film 40 can be a portion of the sensing electrode 41 coated with specific electrolyte materials depending on the type of gases to be sensed.

In accordance with various embodiments of the subject invention, a variety of materials can be used for the sensing electrode 41. The sensing electrode 41 can be made from a variety of materials, including metals, and semiconductors. The semiconductor material is preferably a metal oxide or a metal oxide compound. The terms "metal oxide" and "metal oxide compound" are used interchangeably herein to mean a compound having elemental metal combined with oxygen. Examples of metal oxides that are useful in the invention include $SnO_2$, $TiO_2$, TYPd5, $MoO_3$, $ZnMoO_4$ (ZM), $WO_3$, $La_2CuO_4$, and mixtures thereof. The semiconductor materials can include a metal oxide. The metal oxide is preferably $SnO_2$, $TiO_2$, TYPd5, $MoO_3$, or $ZnMoO_4$, where TYPd5 is an acronym defined below. The acronym TYPd5 is used herein to represent a composite prepared by selecting $TiO_2$ (titania), $Y_2O_3$ (yttria) and Pd in a weight ratio of approximately 85:10:5. The electrolyte is preferably an oxygen ion-conducting electrolyte. The oxygen ion-conducting electrolyte can be based on $ZrO_2$, $Bi_2O_3$ or $CeO_2$. Preferred oxygen ion-conducting electrolytes are electrolyte mixtures, the mixtures generally including a base material, such as $ZrO_2$, $Bi_2O_3$ or $CeO_2$ and one or more dopants, such as calcia (CaO) and yttria ($Y_2O_3$) which can function as stabilizers, or some other suitable oxygen ion-permeable material. For example, yttria stabilized zirconia (YSZ) electrolytes can be formed by mixing yttria and $ZrO_2$. Electrolytes that conduct ionic species other than oxygen ions, e.g., halides, are well known in the art and also find utility in the invention for measuring halogen-containing gas species. The choice of material for electrolyte can depend on the component in the gas mixture to be measured. Thus, to measure the concentration of an oxide component, for example, $NO_x$, $CO_x$ or $SO_x$ the electrolyte is preferably an oxygen-ion conducting electrolyte. Preferred oxygen ion-conducting electrolytes are electrolyte mixtures based on zirconia ($ZrO_2$), bismuth oxide ($B_2O_3$), and ceria ($CeO_2$). Practical electrolyte mixtures generally include one or more dopants, such as calcia (CaO) and yttria ($Y_2O_3$), or some other suitable oxygen ion-permeable material.

In a specific embodiment not shown in FIG. 1, a YSZ substrate 52 can have multiple sensing electrodes 41 on one side. Platinum (or other resistive material) elements are on the opposite side of the YSZ substrate, aligned with the electrodes. The sensing electrodes 41 may also be oriented in a symmetric or nonsymmetrical fashion with respect to each other, and they may be staggered. The Platinum (or other resistive material) elements need not be used as heating elements or conductors 30. The Platinum elements may be used as heating elements and/or temperature sensors. In another embodiment, the conductors 30 can be used for cooling of the sensing electrodes 41 via, for example, thermoelectric cooling. The cooling elements or conductors 30 may also be made of any material which allows cooling of specific regions in the device. The thermal characteristics of the heating/cooling elements (conductors 30) and/or surface temperature sensors can be improved with the use of insulating materials integrated into the device structure or by other specific shape or design change to the device that impacts the thermal properties of the device, such as empty volumes. The shape of the substrate 52 can also vary.

Referring to FIG. 1, in some embodiments, the conductors 30 in FIG. 1 extend along the Y direction pointing out from the paper. In some embodiments, the conductors 30 in FIG. 1 extend along the X direction and form a continuous stripe. The two cross sections of the conductors 30 described above can be observed when dissecting the gas sensor 200 from different positions. The conductors 30 described herein may include metals with high melting temperatures such as W, Pt, Ta, semiconductors such as single/poly silicon, or III-V materials.

In some embodiments, sensing electrode 41 can be made from metals (e.g., Platinum), semiconductors (e.g. semiconducting oxides such as $La_2CuO_4$ or $WO_3$), or other material showing sensitivity to a gas. In general, any given sensing electrode material will have varying sensitivity and selectivity to different gas species depending on the temperature of the electrode. The degree to which sensitivity and/or selectivity that changes depends on the material, gas, and temperature. Each electrode may be part of one or more "electrode-pairs". This means that the measurable number of signals can be larger than the actual number of sensing electrodes. Specifically, the design of the sensor array can include (either as individual devices or together in a single device) two different "electrode-pair" schemes. One scheme can use multiple materials at the same time, which may be kept at the same and/or different temperature. The control of the temperature can be accomplished via heating and/or cooling techniques. A device may also incorporate multiple electrodes of the same material that are maintained at one or more different temperatures. Electrodes of the same material may be kept at the same temperature, one or more other features of the electrodes, such as microstructure, size, or thickness, can be different for different electrodes. Accordingly, the gas sensor arrays may utilize one or more of these schemes in a single device, depending on the application.

Referring to FIG. 1, the gas sensors 200 can incorporate specifically designed heating elements or conductors 30 to control the temperature topside of individual sensing electrodes. In an embodiment, the sensing electrodes 41 and the heating elements or conductors 30 are on the top side of the substrate 52. In another embodiment, the sensing electrodes 41 are on both sides of the substrate (not shown). The substrate 52 can be, for example, a YSZ substrate or coated with other electrolyte. The substrate 52 may also be a structural support, such as $Al_2O_3$, with an electrolyte layer on top. In some embodiments, the substrate 52 can be made of metallic or semi conductive materials. The heating elements or conductors 30 can act as resistors and produce heat via Joule heating, by passing electrical current therethrough.

The temperature control of the gas sensor 200 can be important. Precise control of temperature with minimal fluctuations can allow the gas sensor 200 to produce stable sensing signals. Therefore, thermal modeling can be performed during the design phase to provide information regarding the temperature profile in the device for different locations of the sensing electrodes and the heating electrodes on the substrate of the array. For example, platinum can be used for the fabrication of heating elements or conductors 30. Platinum is an industry standard for high-temperature resistance-temperature-devices (RTD) and as heating elements or conductors 30 in gas sensors because of durability and chemical and thermal stability. However, other materials described above may be used as heating elements or conductors 30 in the subject devices.

Referring to FIG. 1, a set of conductors 30 forms a unit and can be designed to control an array with predetermined amount of sensing electrodes 41. Viewing from a top perspective, a unit of the conductors 30 may form a particular pattern with a plurality of openings. Details of the pattern are further discussed in FIG. 4 to FIG. 12 herein. Normally a width W1 of a unit of the conductors 30 is wider than a width W2 of a sensing electrode 41 in order to provide precise temperature control. In some embodiments, a width W1 of a unit of the conductors 30 is in a range of from about 20 to about 2500 micrometer. A width W2 of a single sensing electrode can be in a range of from about 10 to 2000 micrometer. In some embodiments, the conductors 30 are embedded in an insulator 50. That is, the conductors 30 can be positioned in any location in the insulator 50 according to various applications. For example, as shown in FIG. 1, a thickness T2 in the insulator 50 separates the sensing electrodes 41 and the conductors 30. In some embodiments, the thickness T2 is about 5 times than a thickness T1 of the conductors 30. In other embodiments, thickness T2 can be reduced to zero, rendering the conductors 30 coplanar with the top surface S51 of the insulator 50. In still other embodiments, thickness T2 can be increased to a total thickness of the insulator 50 minus the thickness T1, rendering the conductors 30 coplanar with the bottom surface S52 of the insulator 50.

Figure 2:
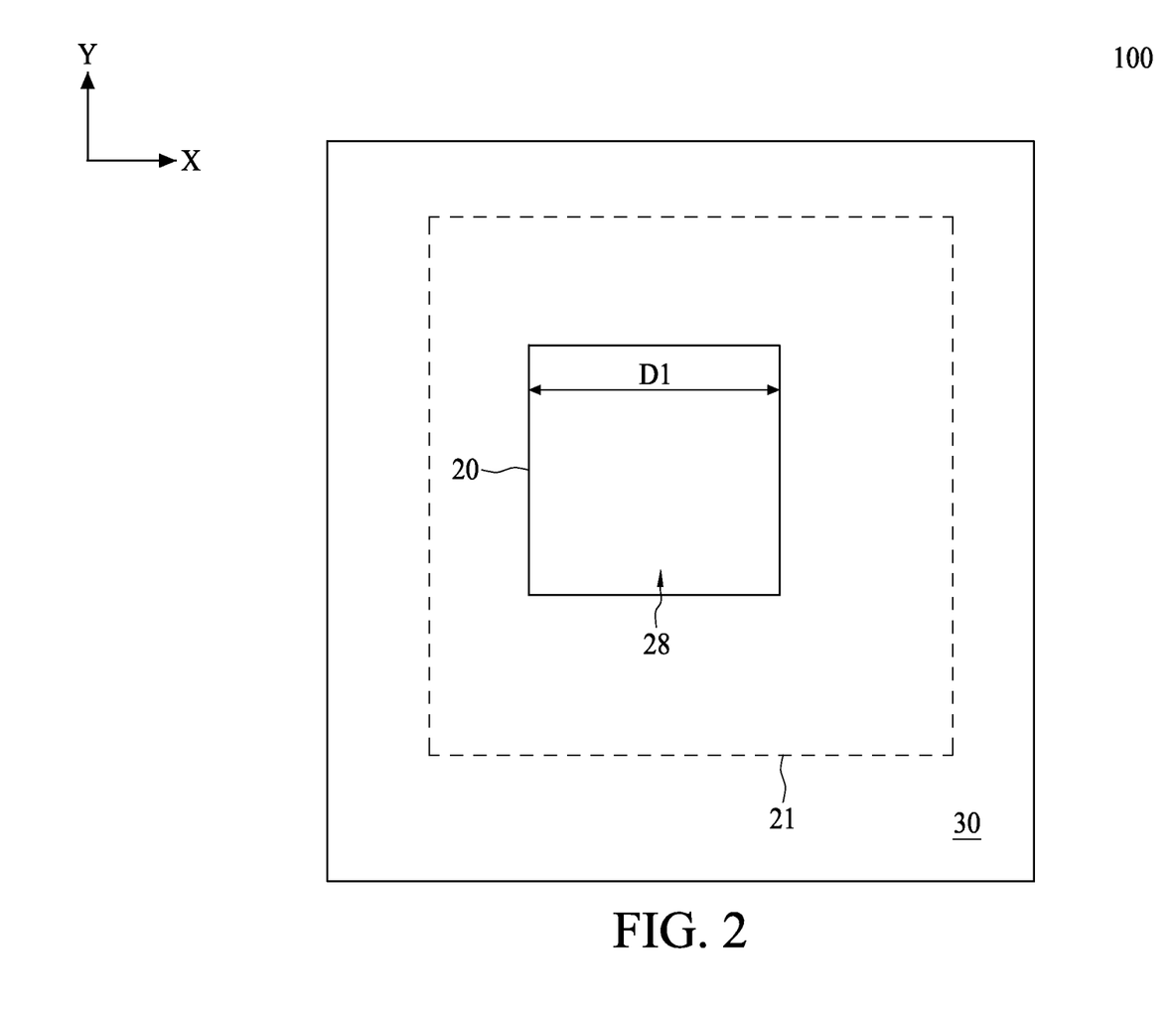
FIG. 2 is a top-view pattern of a heating element, in accordance with some embodiments of the present disclosure.

FIG. 2 is a top-view pattern of a heating element or conductors 30, in accordance with some embodiments of the present disclosure. In some embodiments, a unit of the conductors 30 is composed of a particular pattern 21. FIG. 2 only shows a repeatable feature of the top-view pattern. As shown in FIG. 2, the repeatable feature of the pattern 21 includes an opening 28 defined by a perimeter 20. The opening 28 is formed in the conductor 30 and having a width D1 of about or less than 4 micrometer. The dimension less than 4 micrometer is calculated based on current gas sensor integrated in an IoT system such as in a portable device. The scale of each element in the portable device is shrinked to fit the given capacity.

Figure 3:
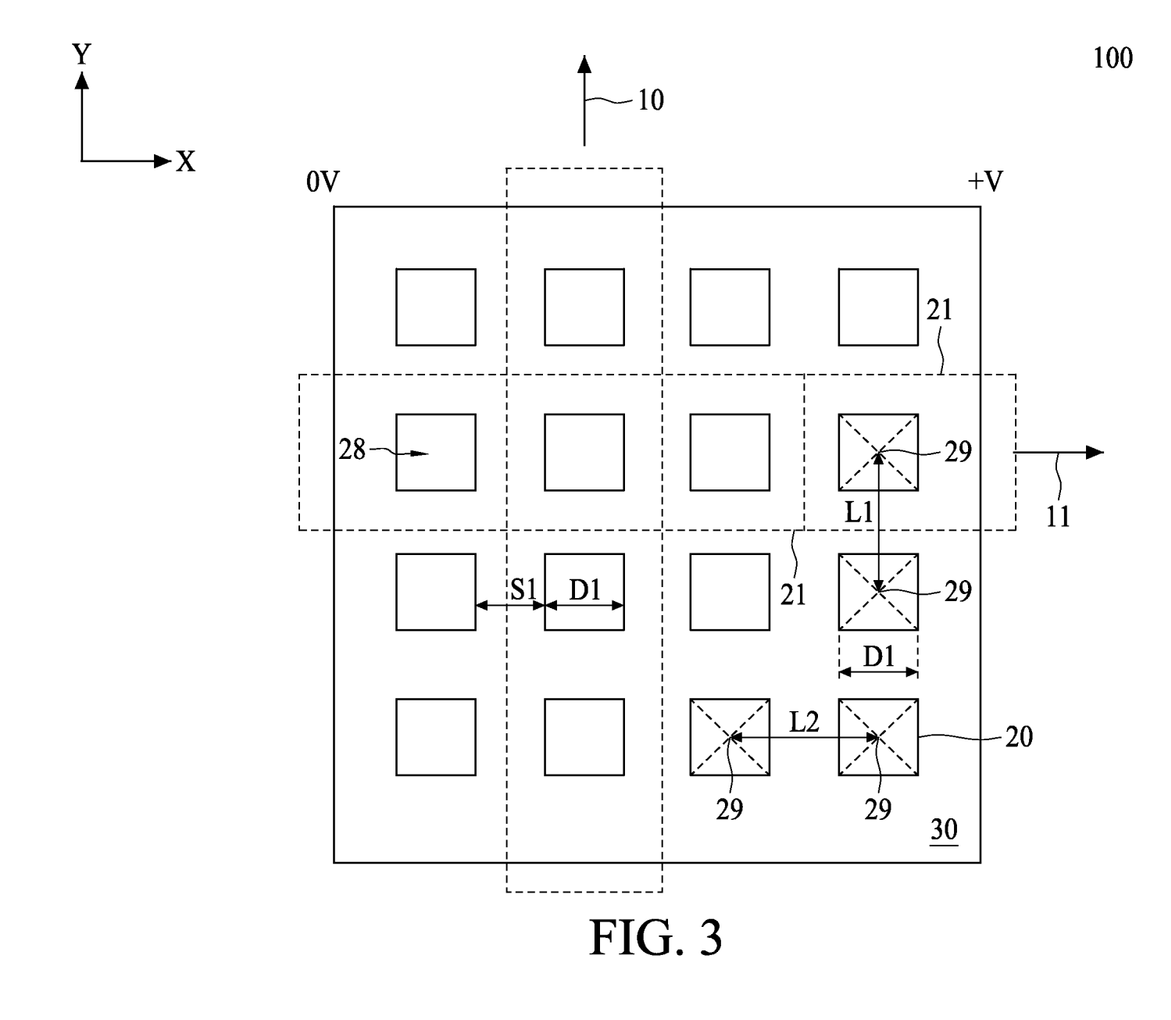
FIG. 3 is a top-view pattern of a heating element, in accordance with some embodiments of the present disclosure.

FIG. 3 is a top-view pattern of a unit of a heating element or a conductor 30, in accordance with some embodiments of the present disclosure. FIG. 3 includes a plurality of repeatable features in FIG. 2 and form a unit of a heating element 100. In FIG. 3, a minimal distance S1 between two adjacent openings 28 is less than about 4 micrometer. The distance S1 is measured between perimeters 20 enclosing adjacent openings 28. The patterns 21 of the heating element repeat in at least two directions, for example, as shown in FIG. 3, the patterns 21 repeat in Y direction 10 and in X direction 11. The opening 28 of the unit of heating element 100 is a square shape. A geometric center 29 of the opening 28 can be defined in each opening 28 in the heating element 100. In some embodiments, a pitch L1 between two geometric centers 29 is identical to a pitch L2 between two geometric centers 29. However, the two pitches described above may not be identical. However, a minimal pitch between two geometric centers 29 is less than about 4 micrometer. In FIG. 3, a low voltage (exemplified as 0V) may connect to one corner of the heating element 100 whereas a high voltage (exemplified as +V) connects to another corner.

The shape of heating element 30 is important to the temperature distribution. In an embodiment, the temperature of the sensing electrode 41 is uniform, or, if desired, nonuniform in a preferred manner. The heating elements can be controlled either by an applied voltage or current. The method of controlling the heating elements utilized depends on the application. As an example, in an automobile, the automobile's battery can be the power source, such that the heating elements 30 would be voltage controlled. Heating elements 30 can be utilized to modify the temperature of the sensing electrodes 41 when needed. The heating elements 30 can be on the opposite side of a substrate from the sensing electrodes (not shown), each appropriately aligned with a specific sensing electrode. Heating elements 30 can be located on the same side of the substrate as the sensing electrodes as well. Heating elements 30 may also be embedded in or on the sensing electrodes 41.

Figure 4A:
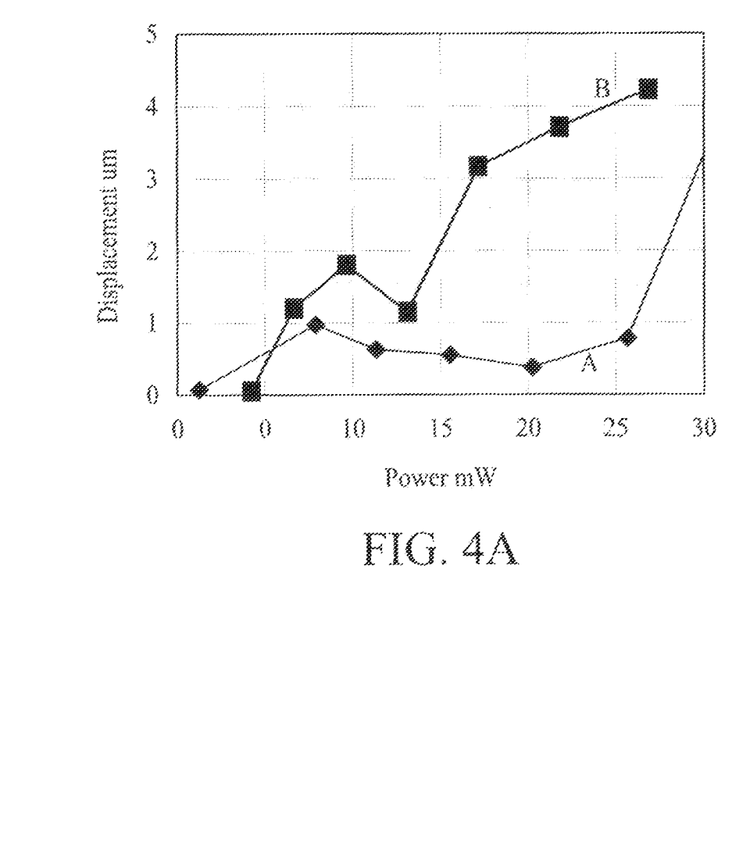
FIG. 4A is a diagram showing degrees of displacement of a conductor as a function of input power of a conventional heating element pattern and a pattern disclosed herein, in accordance with some embodiments of the present disclosure.

FIG. 4A is a diagram showing degrees of displacement of a conductor as a function of input power of a conventional heating element pattern and a pattern disclosed herein, in accordance with some embodiments of the present disclosure. As shown in FIG. 4A, under an input power of 25 mW, a displacement less than 1 micrometer is obtained in the "A" heating element whereas a displacement about 4 micrometer is obtained in the "B" heating element. Note the "A" heating element refers to those embodiments disclosed in the present disclosure and the "B" heating element refers to those conventional serpentine-shaped, a C-shaped, and a spiral-shaped heating element previously discussed.

Figure 4B:
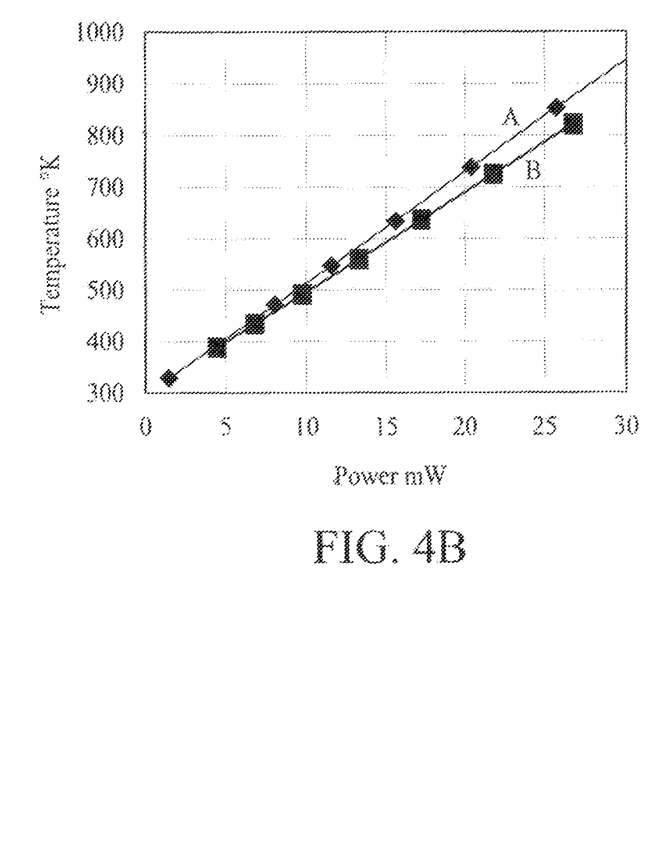
FIG. 4B is a diagram showing a temperature measured at the sensing region as a function of the input power of a conventional heating element pattern and a pattern disclosed herein, in accordance with some embodiments of the present disclosure.

FIG. 4B is a diagram showing a temperature measured at the sensing region as a function of the input power of a conventional heating element pattern and a pattern disclosed herein, in accordance with some embodiments of the present disclosure. As shown in FIG. 4B, under the same input power of 25 mW, the temperature in proximity to the sensing region of the gas sensor disclosed herein is about the same to those conventional gas sensor. It shows that although the reduction in the dimension (e.g., the line width and the pitch) of the heating element, the achieved effect (e.g., temperature control) remains the same but with less displacement.

It should be noted that the heating elements or conductors described in the present disclosure possesses either a minimal dimension in the opening to be less than 4 micrometer or a minimal distance between two adjacent perimeters to be less than about 4 micrometer, or both. The design for the opening and/or a distance between adjacent perimeters having a dimension less than about 4 micrometer provides a result showing in FIG. 4A and FIG. 4B discussed above, that is, the displacement of the heating element or conductors can be effective reduced under the same input power while maintaining a same heating efficiency.

Figure 5:
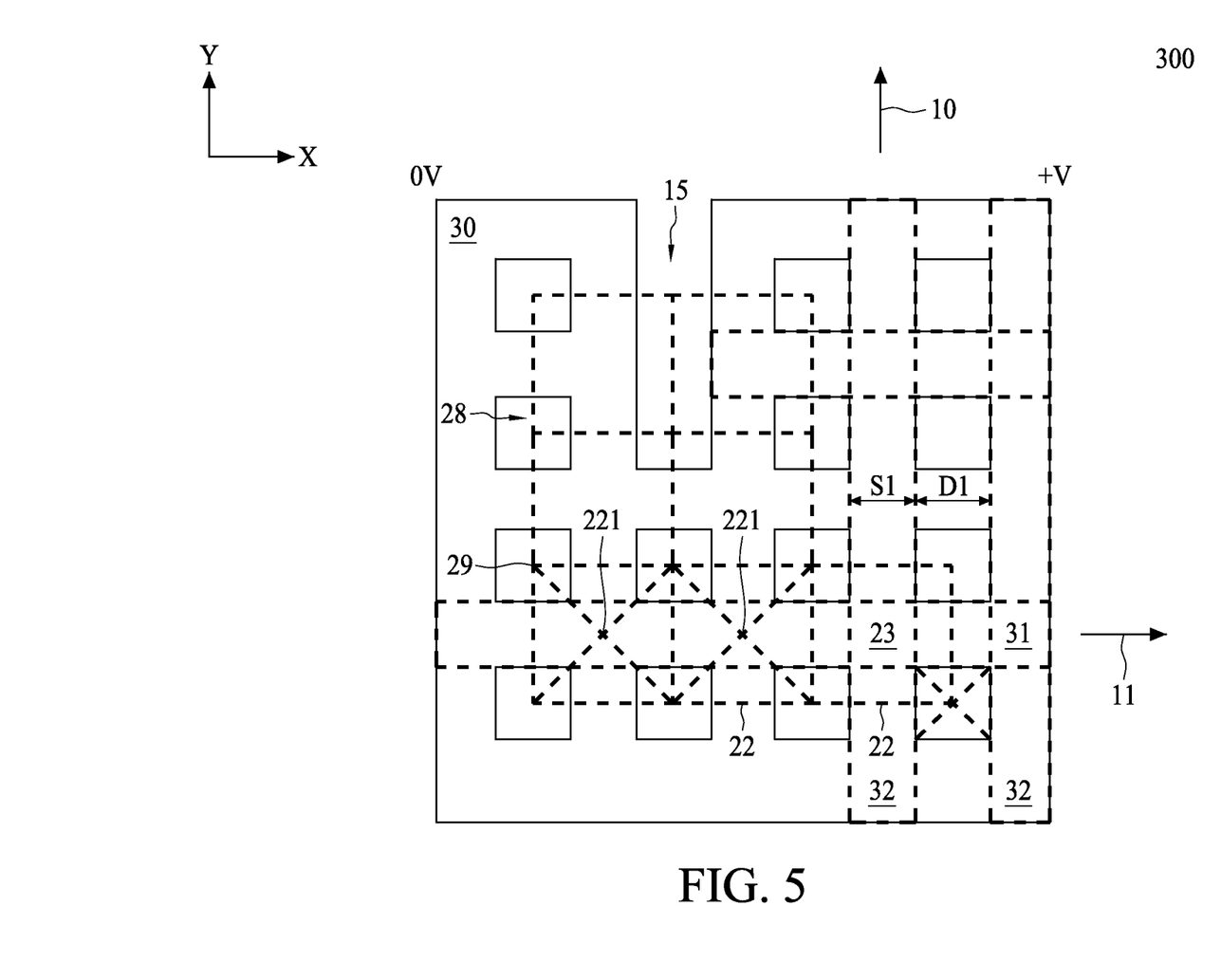
FIG. 5 to FIG. 8 are top-view patterns of a heating element, in accordance with some embodiments of the present disclosure.

FIG. 5 to FIG. 8 are top-view patterns of a heating element, in accordance with some embodiments of the present disclosure. In FIG. 5, a unit of a heating element 300 is shown. The heating element 300 is shown in a top view perspective, including a plurality of segments 31 and 32 intersecting with each other. Intersection 23 formed by staggered segments 31 and 32 can be located. A plurality of patterns 22 can be identified in FIG. 5. For example, the pattern 22 includes four one-quarter openings 28 at the four corners of the pattern 22 and an intersection 23 in the middle of the pattern 22. The pattern 22 is arranged in a repeating manner along, for example, a first direction 11 (e.g., X direction), and a second direction 10 (e.g., Y direction) orthogonal to the first direction. In FIG. 5, each segment 31 or 32 may have identical width. For example, a minimal width S1 of the segment 31 or 32 is less than 4 micrometer. In addition, a minimal distance D1 across the opening 28 is less than about 4 micrometer. In some embodiments, the minimal distance D1 in the opening 28 is measured between two parallel segments 32 adjacent to each other. A geometric center 221 in each pattern 22 can be located in the middle of the pattern 22. In FIG. 5, a four-fold symmetry can be identified with respect to the geometric center 221. An impedance adjusting portion 15 is illustrated in the heating element 300. In order to design and alter the overall impedance of the circuitry, the repeating pattern 22 can be interrupted with a greater opening (i.e., less conductive materials) in the heating element 300. For example, the impedance adjusting portion 15 interrupts the pattern 22 described above and forms an opening occupying four times of a distance D1 of the opening 28.

Figure 6:
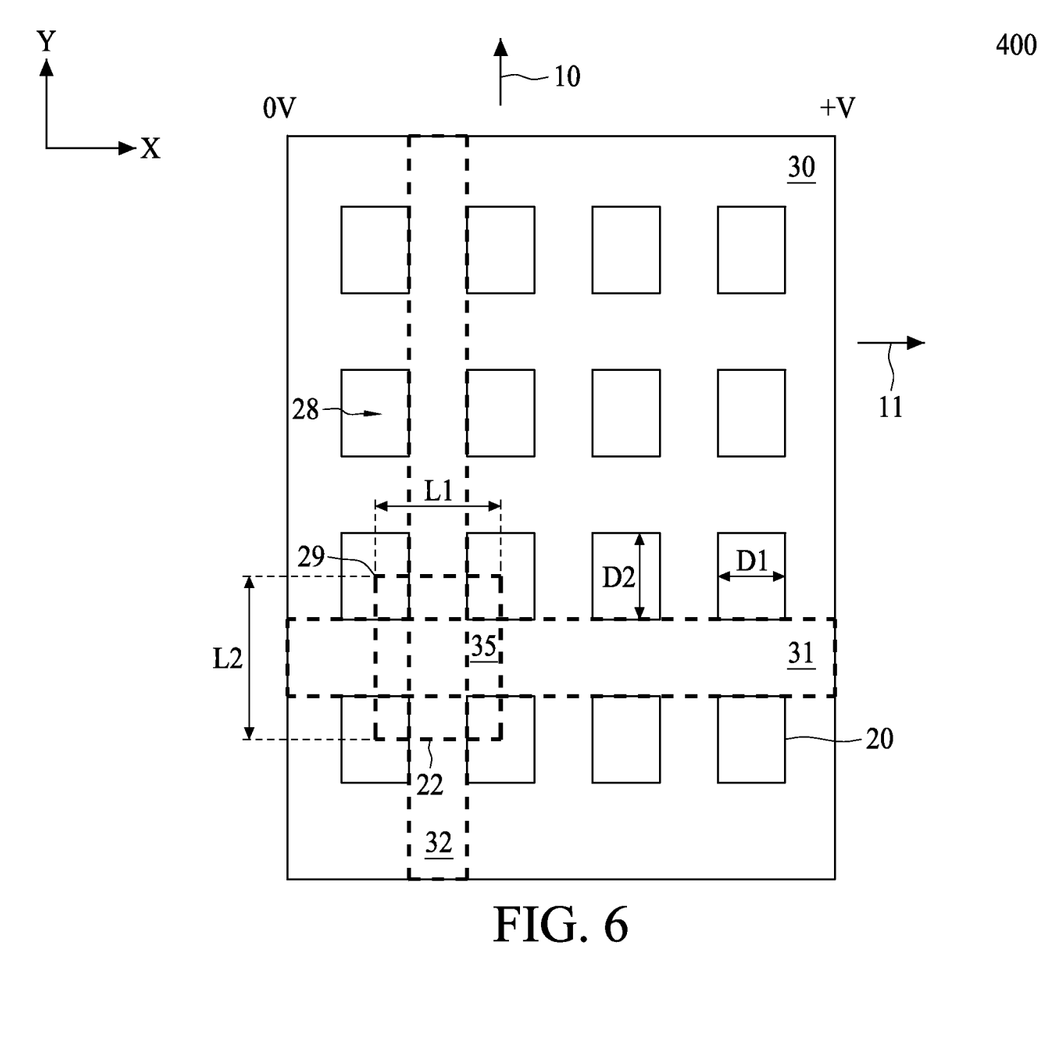

In FIG. 6, a unit of a heating element 400 is shown. The heating element 400 is shown in a top view perspective, including a plurality of segments 31 and 32 intersecting with each other. Intersection 35 formed by staggered segments 31 and 32 can be located. A plurality of patterns 22 can be identified in FIG. 6. For example, the pattern 22 includes four one-quarter openings 28 at the four corners of the pattern 22 and an intersection 35 in the middle of the pattern 22. The pattern 22 is arranged in a repeating manner along, for example, a first direction 11 (e.g., X direction), and a second direction 10 (e.g., Y direction) orthogonal to the first direction. In FIG. 6, each segment 31 or 32 may have identical width. For example, a minimal width S1 of the segment 31 or 32 is less than 4 micrometer. In addition, due to the opening 28 having a tetragonal shape, a distance D1 is smaller than a distance D2 in the opening 28. In some embodiments, the minimal distance D1 in the opening 28 is less than about 4 micrometer. In some embodiments, the minimal distance D1 in the opening 28 is measured between two parallel segments 32 adjacent to each other.

Figure 7:
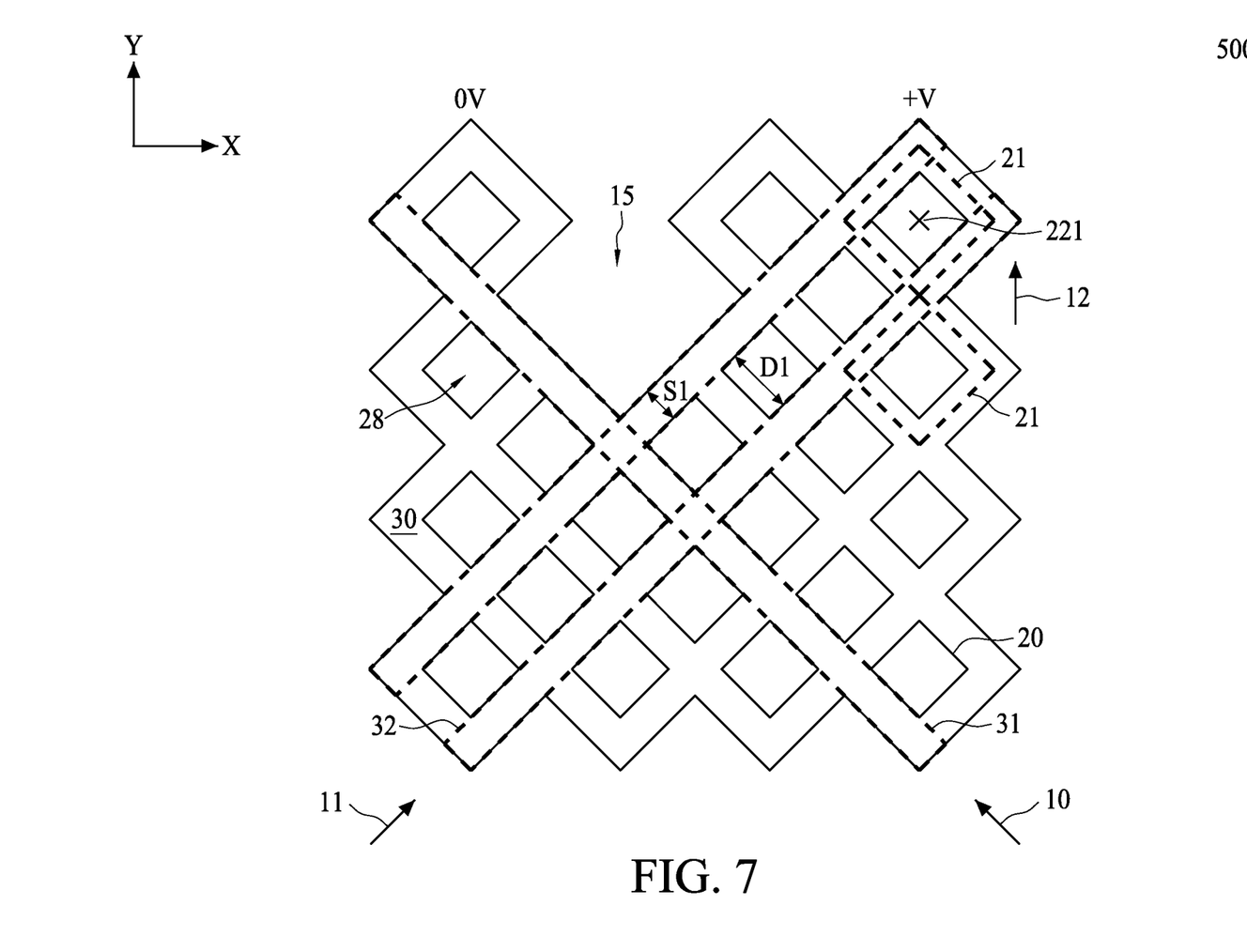

In FIG. 7, a unit of a heating element 500 is shown. The heating element 500 is shown in a top view perspective, including a plurality of segments 31 and 32 intersecting with each other. A plurality of patterns 21 can be identified in FIG. 7. For example, the pattern 21 includes four one-one opening 28 defined by the perimeter 20. The pattern 21 is arranged in a repeating manner along, for example, a first direction 11, a second direction 10 orthogonal to the first direction, and a third direction 12. In FIG. 7, each segment 31 or 32 may have identical width. For example, a minimal width S1 of the segment 31 or 32 is less than 4 micrometer. In addition, a minimal distance D1 across the opening 28 is less than about 4 micrometer. In some embodiments, the minimal distance D1 in the opening 28 is measured between two parallel segments 32 adjacent to each other. An impedance adjusting portion 15 is illustrated in the heating element 500. The impedance adjusting portion 15 interrupts the pattern 21 described above and forms an opening occupying an area of four patterns 21. In FIG. 7, the center 29 of the opening 28 and a geometric center 221 of the pattern 21 are overlapped.

Figure 8:
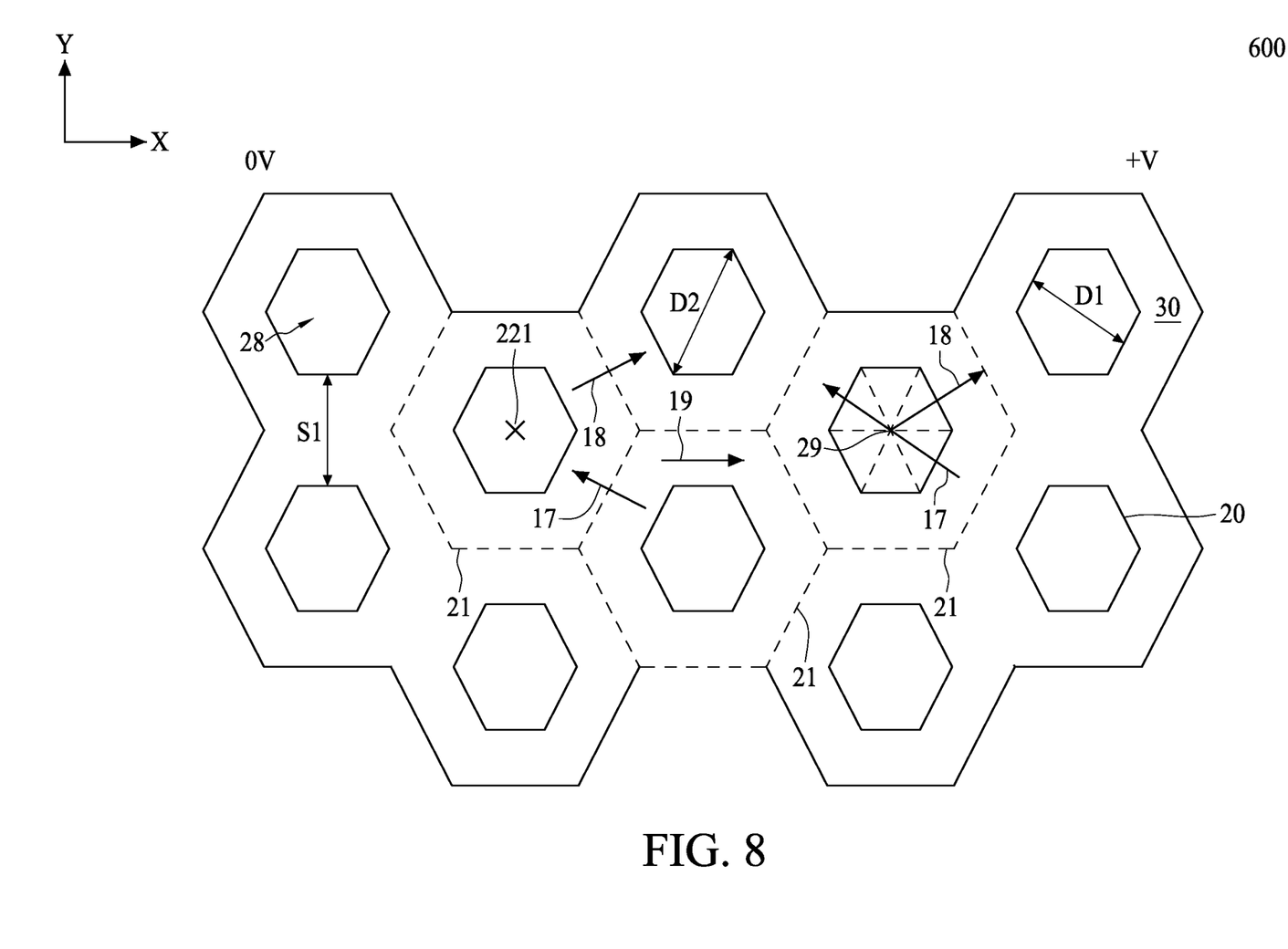
Figure 9:
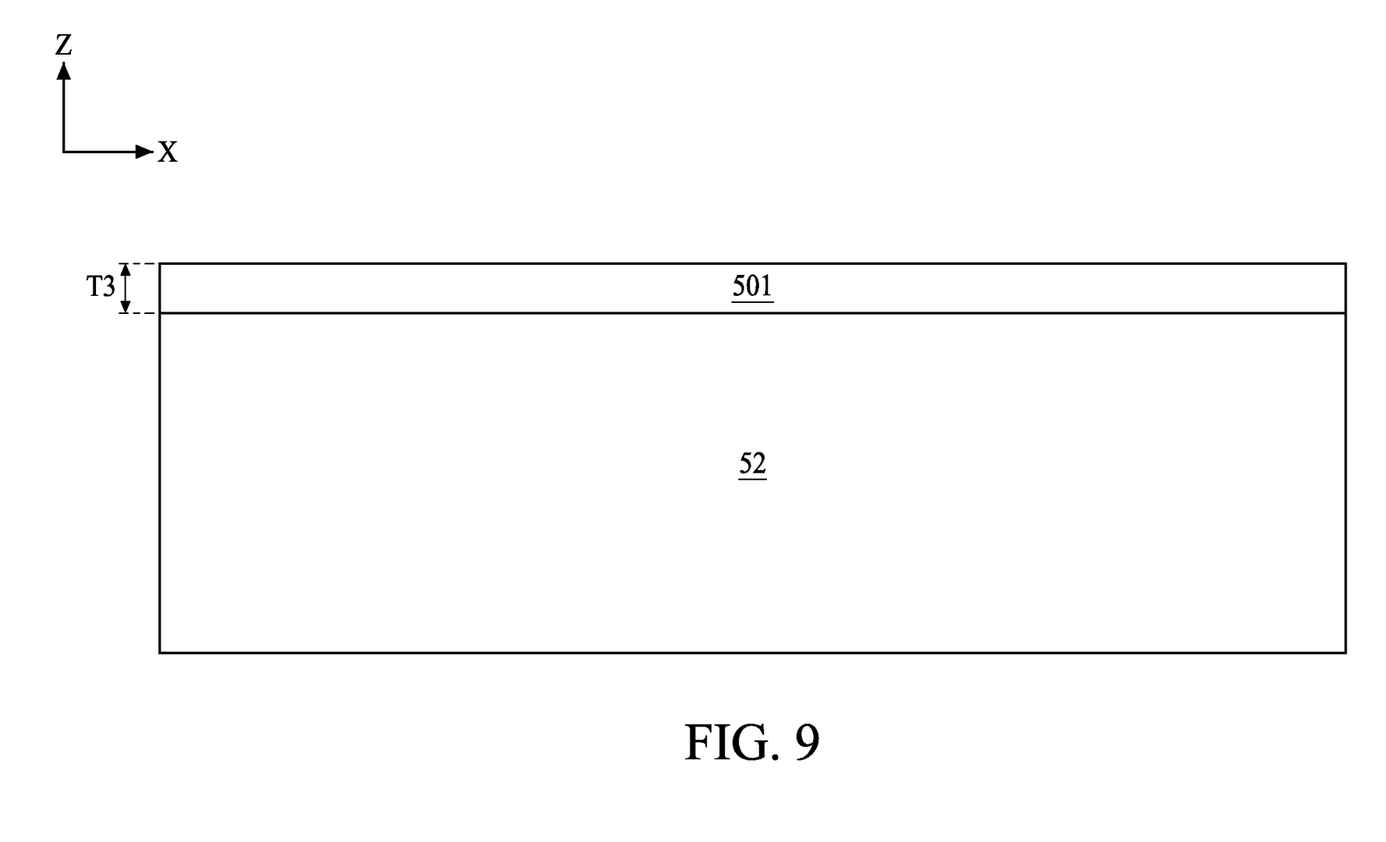
FIG. 9 to FIG. 13 are fragmental cross sectional views of a method manufacturing a heating element described herein, in accordance with some embodiments of the present disclosure.

In FIG. 8, a unit of a heating element 600 is shown. The heating element 600 is shown in a top view perspective, including a conductor 30 having a hexagonal pattern 21 with an opening 28. The patterns 21 of the heating element 600 repeat in at least three directions, for example, as shown in FIG. 8, the patterns 21 repeat in a first direction 17, a second direction 18, and a third direction 19 (i.e. the X direction). Note the first direction 17 is not orthogonal to the second direction 18. The opening 28 of the unit of heating element 600 is a hexagonal shape. A geometric center 29 of the opening 28 can be defined. In some embodiments, a first distance D1 between opposite sides of the perimeter 20 is shorter than a second distance D2 between opposite vertices of the perimeter 20 in the opening 28. A minimal distance D1 of the opening 28 is less than about 4 micrometer. In FIG. 8, the center 29 of the opening 28 and a geometric center 221 of the pattern 21 are overlapped FIG. 9 to FIG. 13 are fragmental cross sectional views of a method for manufacturing a heating element described herein, in accordance with some embodiments of the present disclosure. In FIG. 9, a substrate 52 for a gas sensor is provided. As previously discussed the substrate 52 can undergo an operation of forming pores or cavities therein in order to reduce the thermal conductivity of the substrate 52. An insulating layer 501 is subsequently formed over the substrate 52. A thickness T3 of the insulating layer 501 is predetermined according to various design factors. In some embodiments, the thickness T3 determines a distance between the conductor 30 and the substrate 52.

Figure 10:
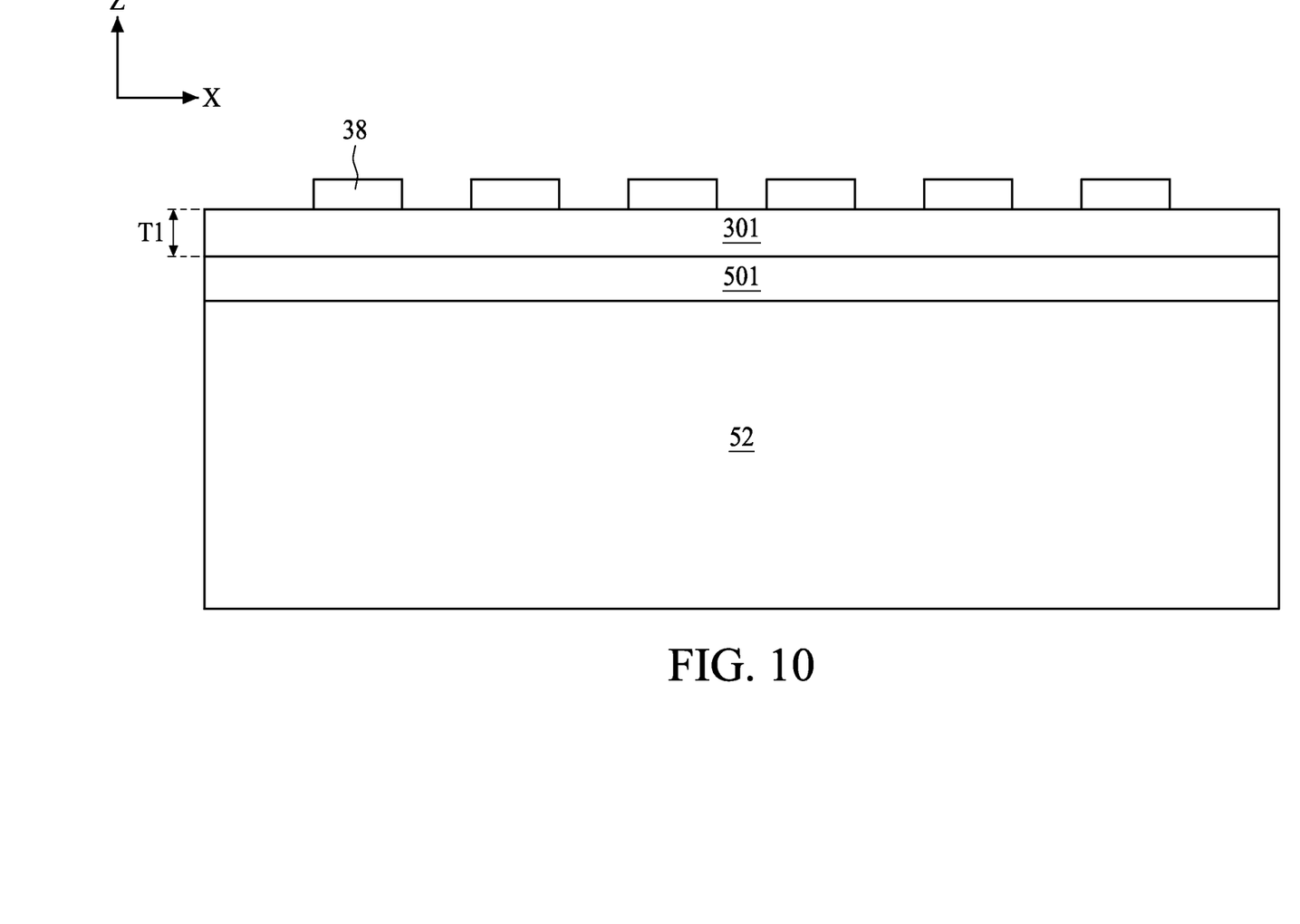
Figure 11:
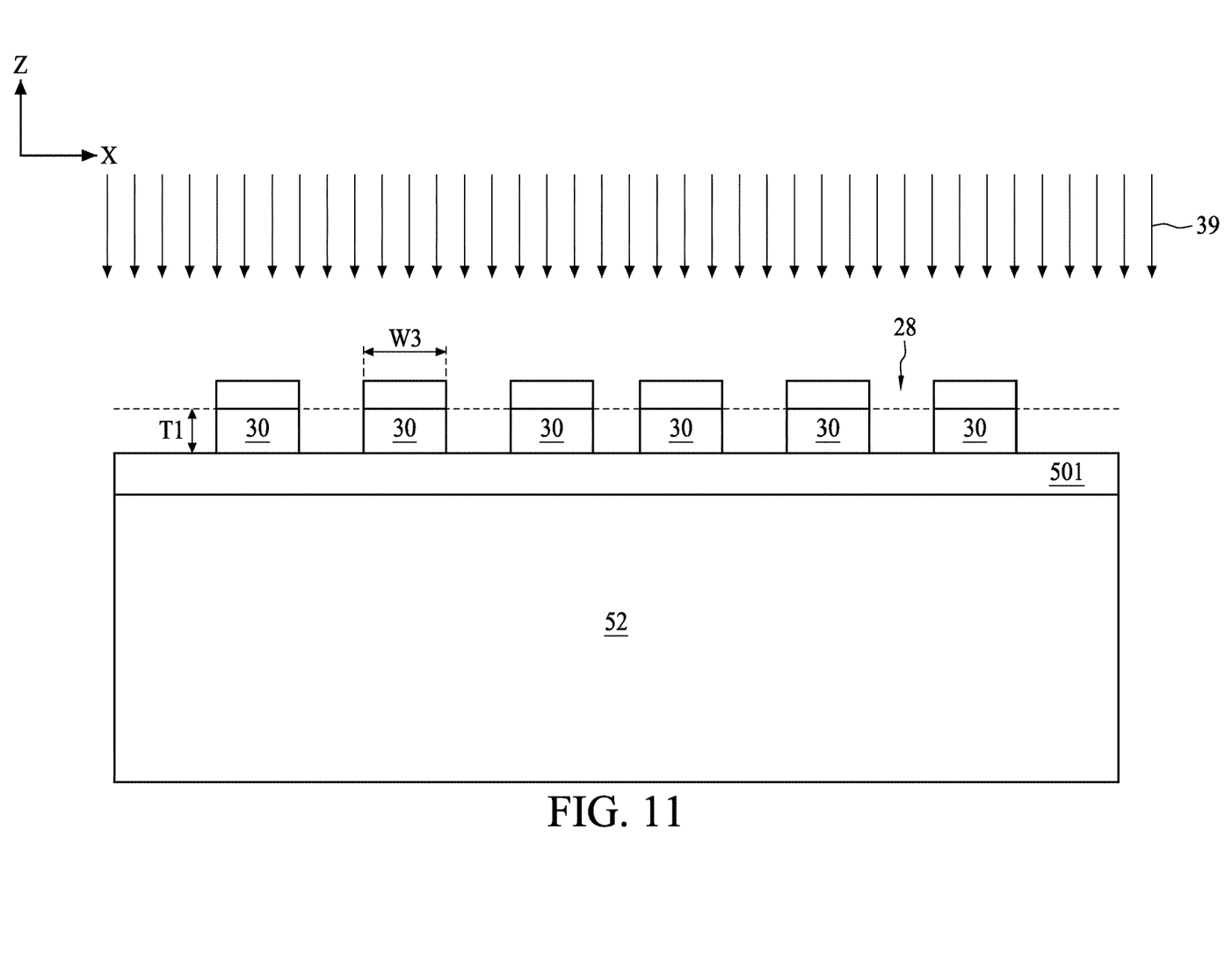

In FIG. 10, a conductor layer 301 is deposited over the insulating layer 501. In some embodiments, a thickness T1 of the conductor layer 301 is in a range of from about 0.1 to about 1 micrometer. Note the thickness of the conductor 30 may be thinner than a width of a segment of the conductor described above. A mask layer 38 is then formed and patterned over the conductor layer 301 in order to transfer the pattern with repeating features to the conductor layer 301. In FIG. 11, an etching operation is conducted over the conductor layer 301 to form the pattern with repeating features. In some embodiments, the pattern with repeating features includes all the embodiments described above. In some embodiments, the pattern with repeating features includes a plurality of openings. The openings may include various dimensions measured by different fashions. However, the openings formed in the present disclosure are designed to have a minimal dimension of about 4 micrometer. In some embodiments, the openings can have a circular or a polygonal shape.

Referring to FIG. 11, a dry etching operation 39 is conducted to form the openings. In some embodiments, an inductively-coupled plasma with at least the etching gas $SF_6$ and under a power or 10 to 1000 W is used. Viewing from a top-view perspective, sidewalls 30a of each segment of the conductor 30 form a perimeter 20 defining the opening 28. In some embodiments, the sidewall 30a of each segment is substantially vertical. Referring back to FIG. 5 and FIG. 6, the perimeter includes a symmetrical shape such as a square shown in FIG. 5 or an elongated shape such as a tetragonal shape shown in FIG. 6. Moreover, a geometric center can be defined in each symmetrical or elongated openings defined by the perimeters. Referring back to FIG. 5 for example, an impedance adjusting portion 15 is also formed in the pattern of the conductor 30. The relative position and dimension of the impedance adjusting portion 15 in each heating element is predetermined at the mask layer patterning operation discussed in FIG. 10.

Figure 12:
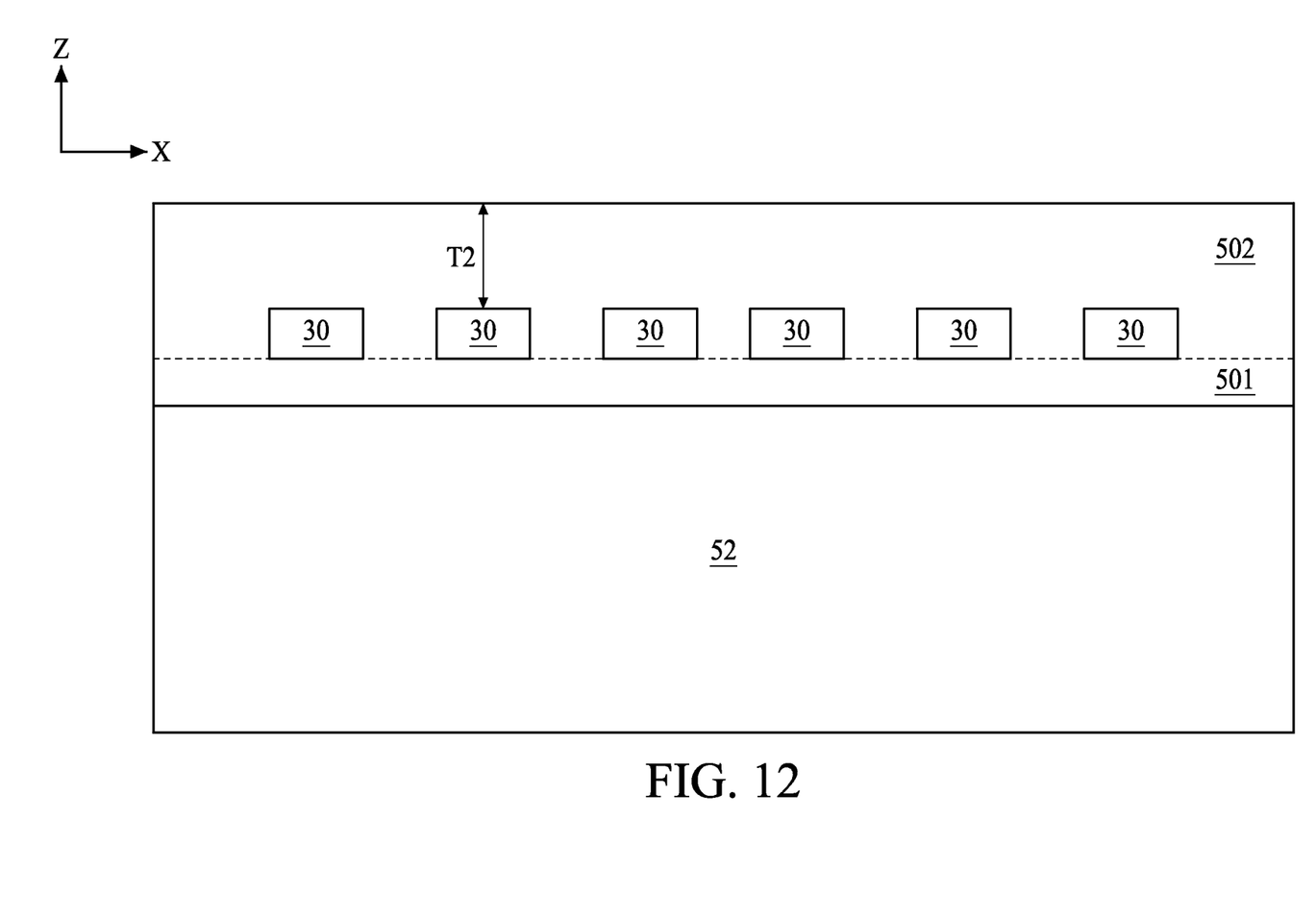
Figure 13:
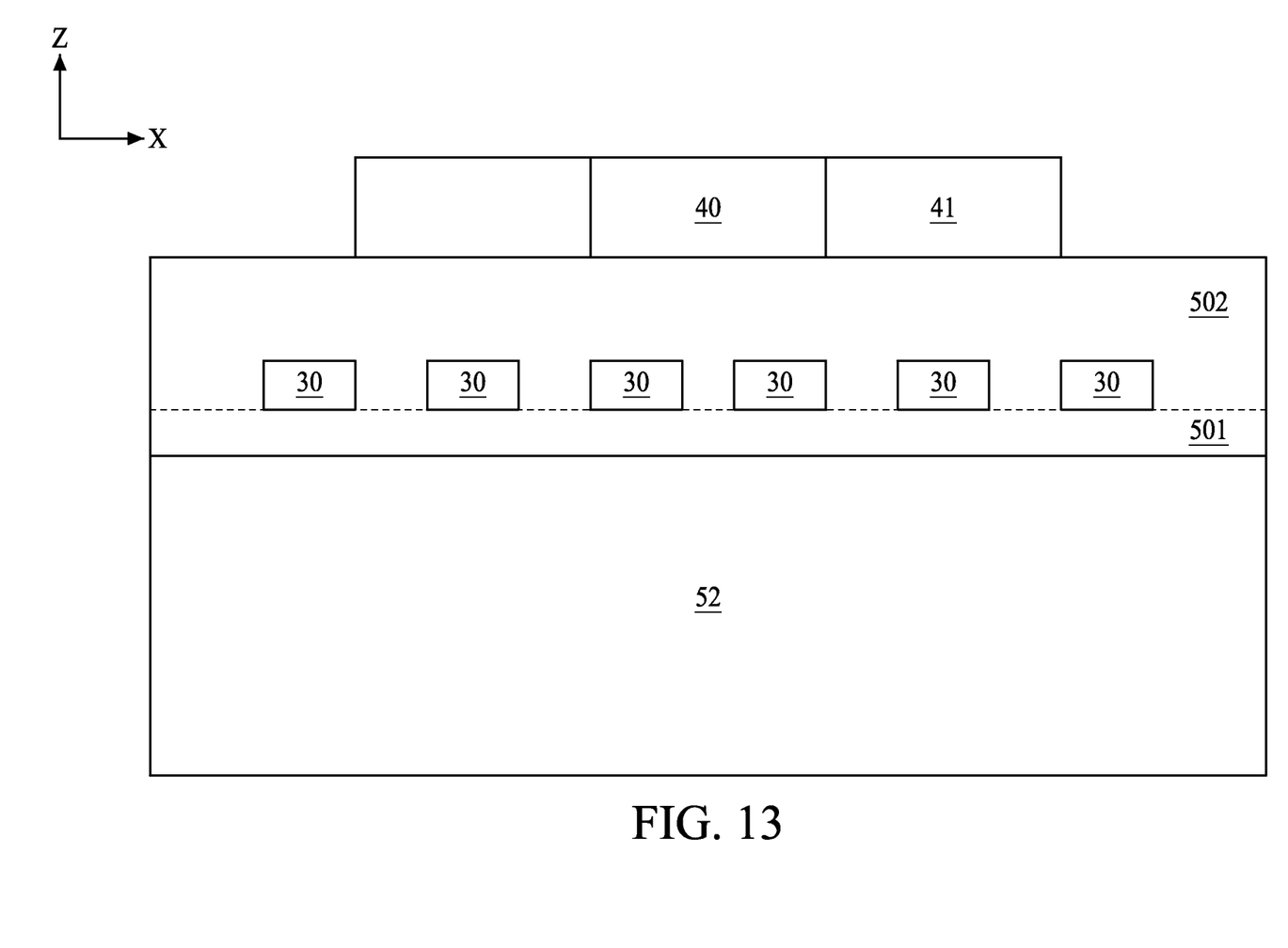

Referring to FIG. 11, at the time of forming the openings 28 by an etching operation, the remaining conductors 30 shows a plurality of segments staggering with each other. As discussed above, a width W3 of each segment is below or about 4 micrometers. In FIG. 12, the mask layer 38 is removed and another insulating layer 502 is formed by filling the openings of the conductors 30 and depositing over a top surface of the conductor 30. In some embodiments, a thickness T2 measured from the top surface of the conductor 30 to a bottom of the gas sensing region is determined to be about 5 times of the thickness T1. For example, the thickness T2 is in a range of from about 0.5 to about 5 micrometer. The thickens T2 is a design factor considering the thermal power of the heating element or the conductor 30 and the thermal conductivity of the insulating layer 502 with respect to the gas sensing region. In FIG. 13, a gas sensing film 40 and sensing electrodes 41 are formed over the insulating layer 502. In some embodiments, thickness T2 can be zero or thickness T3 can be zero.

In an embodiment of the present invention, a portable gas sensor such as a portable alcohol analyzer, a portable leaking gas sensor, a portable breath analyzer is provided. A user can conveniently use a gas which can be easily obtained, e.g., a human breath or air, as a substitutionary reference gas. Typically, the semiconductor gas sensor has reactivity to various gases such like CH-based gas, $H_2O$, CO, $SO_2$, $H_2S$, and HCHO. However, the reactivity of each semiconductor gas sensor is slightly different from each other depending on catalysis and temperature. This fact enables the semiconductor gas sensor to sense a particular gas. Based on this useful and unique characteristic of the semiconductor gas sensor, the inventive portable gas sensor is developed. The heating element devised in the portable gas sensor is designed to have a particular pattern with repeating features and with dimensional constraints in terms of the minimal dimension of the openings and a width of the heat-generating segments. With the appropriate etching technique disclosed herein, the heating element can achieve milder displacement or deformation due to Joule heating and at the same time, provide sufficient thermal power to the gas sensing region in a portable device.

Some embodiments of the present disclosure provide a gas sensor in an IOT. The gas sensor includes a substrate, a conductor disposed above the substrate, and a sensing film disposed over the conductor. The conductor has a top-view pattern including a plurality of openings, a minimal dimension of the opening being less than about 4 micrometer; and a perimeter enclosing the opening.

In some embodiments, the gas sensor further includes a minimal distance between two adjacent perimeters, the minimal distance being less than about 4 micrometer.

In some embodiments, the pattern of the conductor is repeated in at least two directions.

In some embodiments, the substrate of the gas sensor is composed of metal or semiconductor.

In some embodiments, each of the plurality of openings includes a center, and a minimal pitch of adjacent centers is less than 4 micrometer.

In some embodiments, the conductor of the gas sensor includes impedance adjusting portion between the plurality of openings.

In some embodiments, the substrate of the gas sensor includes cavities.

Some embodiments of the present disclosure provide a heating element in a portable device, including a substrate, a conductor disposed over the substrate. The conductor includes a plurality of segments crossing to form an intersection, and a top-view pattern of the conductor encircling the intersection being arranged in a repeating manner. A minimal width of each of the plurality of segments is less than about 4 micrometer.

In some embodiments, the heating element further includes a minimal dimension between the segments parallel with each other, the minimal dimension being less than about 4 micrometer.

In some embodiments, the top-view pattern of the heating element is repeated in at least two orthogonal directions.

In some embodiments, the intersection of the conductor is disposed at a center of the top-view pattern.

In some embodiments, the top-view pattern includes a geometric center.

In some embodiments, the heating element further includes impedance adjusting portion in the conductor, discontinuing the top-view pattern.

In some embodiments, the substrate of the heating element includes porous features.

Some embodiments of the present disclosure provide a method of manufacturing a gas sensor. The method includes receiving a substrate; forming a conductor layer, over the substrate; patterning the conductor layer to form a conductor with a plurality of openings by an etching operation, and forming a gas-sensing film over the conductor. The openings are arranged in a repeating pattern, and a minimal dimension of the opening being about 4 micrometer.

In some embodiments, the patterning the conductor to form a plurality of the opening by etching includes forming a polygonal opening.

In some embodiments, the patterning the conductor to form a plurality of the opening by etching includes forming a perimeter defining the opening. The perimeter includes a symmetrical or elongated shape with respect to a geometric center of the opening.

In some embodiments, the patterning the conductor to form a plurality of the opening by etching includes forming an impedance adjusting portion in the conductor interrupting the repeating pattern.

In some embodiments, the patterning the conductor to form a plurality of the opening by etching includes forming a segment between the openings. The segment includes a minimal width of about or less than 4 micrometer.

In some embodiments, the patterning the conductor to form a plurality of the opening by etching includes inductively-coupled plasma etch.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A gas sensor in an Internet of Things, comprising:
   a substrate;
   an insulator over a substrate;
   a patterned conductor embedded in the insulator, the patterned conductor comprising a plurality of repeatable patterns from a top view perspective, the repeatable pattern each comprising:
      an opening, a minimal dimension of the opening being less than 4 micrometers; and
   a sensing film disposed over a portion of the insulator.

2. The gas sensor of claim 1, further comprising a distance between two adjacent openings, the distance being less than about 4 micrometer.

3. The gas sensor of claim 1, wherein the repeatable pattern is repeated in at least two directions.

4. The gas sensor of claim 1, wherein the substrate is composed of metal or semiconductor.

5. The gas sensor of claim 1, wherein the opening comprises a geometric center, and a minimal pitch of adjacent centers is less than 4 micrometer.

6. The gas sensor of claim 1, wherein the patterned conductor comprises an impedance adjusting portion between a plurality of the openings.

7. The gas sensor of claim 1, wherein the substrate comprises cavities.

8. A gas sensor, comprising:
   a substrate;
   an insulator over a substrate;
   a conductor disposed over the substrate and embedded in the insulator, the conductor comprising:
      a plurality of segments crossing to form a plurality of intersections; and
      a plurality of repeatable patterns from a top view perspective, the repeatable pattern each comprising:
         an opening enclosed by a portion of the plurality of segments, a minimal dimension of the opening being less than 4 micrometers;
   a sensing film disposed over a portion of the insulator.

9. The gas sensor of claim 8, further comprising a minimal dimension between the segments parallel with each other, the minimal dimension being less than about 4 micrometer.

10. The gas sensor of claim 8, wherein the repeatable pattern is repeated in at least two orthogonal directions.

11. The gas sensor of claim 8, wherein the opening is at a center of the repeatable pattern.

12. The gas sensor of claim 8, wherein the repeatable pattern comprises a geometric center.

13. The gas sensor of claim 8, further comprising an impedance adjusting portion in the conductor, discontinuing the top-view pattern.

14. The gas sensor of claim 8, wherein the substrate comprises porous features.

15. A gas sensor in a portable device, comprising:
   a substrate;
   an insulator over a substrate;
   a patterned conductor embedded in the insulator, and
   a sensing film disposed over a portion of the insulator,
   wherein the patterned conductor comprises a plurality of repeatable pattern from a top view perspective, the repeatable pattern each comprising:
      an opening, a minimal dimension of the opening being less than 4 micrometers; and
   wherein the patterned conductor is configured as a heating element.

16. The gas sensor of claim 15, further comprising a minimal distance between two adjacent openings, the minimal distance being less than about 4 micrometer.

17. The gas sensor of claim 15, wherein the pattern is repeated in at least two directions.

18. The gas sensor of claim 15, wherein the patterned conductor comprises impedance adjusting portion between a plurality of the openings.

19. The gas sensor of claim 18, wherein the impedance adjusting portion discontinues the plurality of repeatable pattern.

20. The gas sensor of claim 15, wherein the patterned conductor comprises platinum.

* * * * *